US008835571B2

(12) United States Patent
Ueno et al.

(10) Patent No.: US 8,835,571 B2
(45) Date of Patent: Sep. 16, 2014

(54) FATTY ACID DERIVATIVE-POLYMER CONJUGATE

(71) Applicant: Sucampo AG, Zug (CH)

(72) Inventors: Ryuji Ueno, Montgomery, MD (US); Peter Lichtlen, Thalwil (CH); Robert Gurny, Geneva (CH); Michael Möller, Saint Cergue (CH)

(73) Assignee: Sucampo AG, Zug (CH)

( * ) Notice: Subject to any disclaimer, the term of this patent is extended or adjusted under 35 U.S.C. 154(b) by 0 days.

(21) Appl. No.: 13/866,714

(22) Filed: Apr. 19, 2013

(65) Prior Publication Data

US 2013/0281637 A1 Oct. 24, 2013

Related U.S. Application Data

(60) Provisional application No. 61/636,122, filed on Apr. 20, 2012.

(51) Int. Cl.
*A61K 31/20* (2006.01)
*A61K 9/107* (2006.01)
*A61K 31/231* (2006.01)
*A61K 47/34* (2006.01)

(52) U.S. Cl.
USPC .......................... 525/450; 525/415; 514/20.8

(58) Field of Classification Search
USPC .................. 525/415, 450; 514/20.8
See application file for complete search history.

(56) References Cited

U.S. PATENT DOCUMENTS

| | | | |
|---|---|---|---|
| 5,001,153 A | 3/1991 | Ueno et al. | |
| 5,073,569 A | 12/1991 | Ueno et al. | |
| 5,106,869 A | 4/1992 | Ueno et al. | |
| 5,151,444 A | 9/1992 | Ueno et al. | |
| 5,166,174 A | 11/1992 | Ueno et al. | |
| 5,166,178 A | 11/1992 | Ueno et al. | |
| 5,194,429 A | 3/1993 | Ueno et al. | |
| 5,212,324 A | 5/1993 | Ueno | |
| 5,221,690 A | 6/1993 | Sugiyama et al. | |
| 5,221,763 A | 6/1993 | Ueno et al. | |
| 5,225,439 A | 7/1993 | Ueno et al. | |
| 5,236,907 A | 8/1993 | Ueno et al. | |
| 5,380,709 A | 1/1995 | Ueno et al. | |
| 5,399,363 A | 3/1995 | Liversidge et al. | |
| 5,428,062 A | 6/1995 | Ueno et al. | |
| 5,466,468 A | 11/1995 | Schneider et al. | |
| 5,534,547 A | 7/1996 | Ueno et al. | |
| 5,543,158 A | 8/1996 | Gref et al. | |
| 5,580,579 A | 12/1996 | Ruddy et al. | |
| 5,591,887 A | 1/1997 | Ueno et al. | |
| 5,629,001 A | 5/1997 | Michael et al. | |
| 5,641,515 A | 6/1997 | Ramtoola | |
| 5,686,487 A | 11/1997 | Ueno | |
| 5,725,871 A | 3/1998 | Illum | |
| 5,739,161 A | 4/1998 | Ueno | |
| 5,756,353 A | 5/1998 | Debs | |
| 5,770,759 A | 6/1998 | Ueno et al. | |
| 5,773,471 A | 6/1998 | Oguchi et al. | |
| 5,780,045 A | 7/1998 | McQuinn et al. | |
| 5,792,451 A | 8/1998 | Sarubbi et al. | |
| 5,804,212 A | 9/1998 | Illum | |
| 5,886,034 A | 3/1999 | Ueno et al. | |
| 6,242,485 B1 | 6/2001 | Ueno | |
| 6,265,440 B1 | 7/2001 | Ueno et al. | |
| 6,613,308 B2 | 9/2003 | Bartus et al. | |
| 2004/0076678 A1* | 4/2004 | Ueno | 424/486 |
| 2009/0281068 A1* | 11/2009 | Moller et al. | 514/152 |
| 2013/0131190 A1* | 5/2013 | Moeller et al. | 514/772.3 |

FOREIGN PATENT DOCUMENTS

| | | |
|---|---|---|
| WO | 2007/012979 A2 | 2/2007 |
| WO | 2012/014011 A1 | 2/2012 |
| WO | WO2012014011 A1 * | 2/2012 ............. C08G 63/78 |

OTHER PUBLICATIONS

Prostaglandins—Wikipedia Entry—Sep. 2002.*
Weinshenker et al. (The Prostaglandins, Chapter 2, Chemistry, p. 5-6, 1973).*
ISR and Written Opinion for Application No. PCT/JP2013/062306 dated Jun. 4, 2013.
Penning et al.; Preparation and properties of absorbable fibres from L-lactide copolymers; Department of Polymer Chemistry, University of Groningen, Nijenborgh 4, NL-9747 AG, The Netherlands (1993); 10 pages.
Uhrich et al.; Polymeric Systems for Controlled Drug Release; Chem Rev. 1999, 99, pp. 3181-3198.
Liu et al.; Polymeric Scaffolds for Bone Tissue Engineering; Annals of Biomedical Engineering, vol. 32, No. 3, Mar. 2004 ((c) 2004) pp. 477-486.
Stock et al.; Tissue Engineering of Cardiac Valves on the Basis of PGA/PLA Co-Polymers; Journal of Long-Term Effects of Medical Implants, 11(3&4): 249-260 (2001).
Mu et al.; A novel controlled release formulation for the anticancer drug paclitaxel (Taxol (r)): PLGA nanoparticles containing vitamin E TPGS; Journal of Controlled Release 86 (2003) pp. 33-48.
Drumright et al.; Polylactic Acid Technology; Advanced Materials, 2000, 12, No. 23, Dec. 1, pp. 1841-1846.
Vink et al.; Applications of life cycle assessment to NatureWorks TM polylactide (PLA) production; Polymer Degradation and Stability 80 (2003) 403-419.
Dechy-Cabaret et al.; Controlled Ring-Opening Polymerization of Lactide and Glycolide; Chem. Rev. 2004, 104, 6147-6176.
Kricheldorf et al.; Polylactones: 31. Sn(II)octoate-initiated polymerization of L-lactide: a mechanistic study; Polymer, vol. 36, No. 6, 1995, pp. 1253-1259.

(Continued)

*Primary Examiner* — Randy Gulakowski
*Assistant Examiner* — Christopher M Rodd
(74) *Attorney, Agent, or Firm* — Sughrue Mion, PLLC

(57) ABSTRACT

A fatty acid derivative-polymer conjugate including a conjugate comprising a fatty acid derivative and an alkyl substituted polylactide compound is provided. A pharmaceutical composition comprising the conjugate is also provided.

29 Claims, 2 Drawing Sheets

(56) References Cited

OTHER PUBLICATIONS

Schwach et al.; More about the Polymerization of Lactides in the Presence of Stannous Octoate; Journal of Polymer Science: Part A: Polymer Chemistry, vol. 35, 3431-3440 (1997).

Degee et al.; Beneficial Effect of Triphenylphosphine on the Bulk Polymerization of L,L-Lactide Promoted by 2-Ethylhexanoic Acid Tin(II) Salt; Journal of Polymer Science : Part A: Polymer Chemistry, vol. 37, 2413-2420 (1999).

Ryner et al.; L-Lactide Macromonomer Synthesis Initiated by New Cyclic Tin Alkoxides Functionalized for Brushlike Structures; Macromolecules, vol. 34, No. 21, 2001, pp. 7281-7287.

Jamshidi et al.; Thermal characterization of polylactides; Polymer, 1988, vol. 29, December, pp. 2229-2234.

Vert et al.; Bioresorbable Plastic Materials for Bone Surgery; Macromolecular Biomaterials; Library of Congress Cataloging in Publication Data, International Standard Book No. 0-8493-6263-6, Library of Congress Card No. 83-7094, Printed in the United States, CRC Press (1984) pp. 120-143.

Remington's Pharmaceutical Sciences, Pharmaceutical Necessities; Eighteen Edition, Mack Printing Company, 1990, pp. 1289-1329.

Hwang et al.; Gastric Retentive Drug-Delivery Systems; Critical Reviews TM in Therapeutic Drug Carrier Systems, 15(3):243-284 (1998).

Remington's Pharmaceutical Sciences, 15th Edition, 1975, Analgesics and Antipyretics; Ewart A. Swinyard, PhD; pp. 1035-1038.

Remington's Pharmaceutical Sciences; Fifteenth Edition, 1975, chapter 88, pp. 1570-1580.

Takenaga et al.; Microparticle resins as a potential nasal drug delivery system for insulin; Journal of Controlled Release 52 (1988) 81-87.

Interview Form; Rescula (R) Eye Drops 0.12%, Jul. 2010, 50 pages.

Mathiowitz et al.; Biologically erodable microspheres as potential oral drug delivery systems; Nature, vol. 386, Mar. 27, 1997, pp. 410-414.

Jiang et al.; Biodegradable poly(lactic-co-glycolic acid) microparticles for injectable delivery of vaccine antigens; Science Direct, Advanced Drug Reviews, 57, (2005) 391-410.

Cuppoletti et al.; Cellular and molecular effects of unoprostone as BK channel activator; Biochimica et Biophysica Acta 1768 (2007) 1083-1092.

* cited by examiner

Efficiency of unoprostone isopropyl incorporation into MPEG-hexPLA polymer micelles Actual obtained unoprostone isopropyl formulation concentrations for the given target concentrations Unoprostone isopropyl MPEG-hexPLA formulation stability at 4°C over a period of two weeks

FATTY ACID DERIVATIVE-POLYMER CONJUGATE

CROSS-REFERENCE TO RELATED APPLICATIONS

This application claims the benefit of U.S. Provisional Application No. 61/636,122 filed Apr. 20, 2012, the disclosures of which are all hereby incorporated by reference.

TECHNICAL FIELD

The present invention relates to a novel fatty acid derivative-polymer conjugate.

BACKGROUND ART

Biocompatible and biodegradable polylactides/glycolides (PLA/PLGA) have received high attention over the last thirty years in the biomedical field as sutures, implants, colloidal drug delivery systems (Penning et al., 1993; Uhrich et al., 1999), and more recently also in tissue repairing and engineering (Liu and Ma, 2004; Stock and Mayer, 2001) and anti-cancer drug delivery (Mu and Feng, 2003; Jiang et al., 2005). Next to the medical field they are also widely used in the packaging area. As biodegradable "green polymers" they are preferable to the commodity polymers currently used (Drumright et al., 2000; Vink et al., 2003).

There is a crucial need of well-defined polylactide-based materials with advanced properties to fit all the requirements for the different applications. For example, PLA/PLGA homo- and co-polymers synthesized by the well-established ring opening polymerization (ROP) process (Dechy-Cabaret et al., 2004; Kricheldorf et al., 1995; Schwach et al., 1997; Degee et al., 1999; Ryner et al., 2001) have a glass transition temperature (Tg) limited to a range of only 40-60° C. (Jamshidi et al., 1988; Vert et al., 1984), independent of the polymer molecular weight and chemical composition. This combined with interesting mechanical properties makes them suitable in medical applications as biodegradable implants, bone fracture fixation devices, scaffolds for living cells.

These polylactides, however, have significant limitations for drug delivery purposes. For drug delivery purposes, polylactides need to be formulated with organic solvents and administered as solutions or in form of nano- and microparticles, and polylactides cannot be injected on their own. Thus there is a significant need for a polylactide which may be used for drug delivery that does not require the use of an organic solvent or to form nano- and micro-particles.

WO2007/012979 discloses compositions and methods relating to polylactides which may be used for drug delivery which do not require the use of an organic solvent or to form nano- and micro-particles prior to injection. These polylactides may be used, for example, to administer a drug to a subject (e.g., a human patient) parenterally without the use of a solvent. More specifically, WO2007/012979 discloses compositions and methods of preparing a pharmaceutical preparation comprising a drug and an alkyl substituted polylactide; wherein the alkyl substituted polylactide is viscous; and wherein a solvent is not required for said admixing (the cited reference is herein incorporated by reference).

WO2012/014011 discloses compositions comprising polymers prepared by melt polycondensation of one or more substituted or unsubstituted C4-C32 2-hydroxyalkyl acids, method of preparing a pharmaceutical composition comprising thereof, and a method for delivering a bioactive agent to a subject, comprising administering to the subject an effective amount of the composition therein (the cited reference is herein incorporated by reference).

Fatty acid derivatives are members of class of organic carboxylic acids, which are contained in tissues or organs of human or other mammals, and exhibit a wide range of physiological activity. Some fatty acid derivatives found in nature generally have a prostanoic acid skeleton as shown in the formula (A):

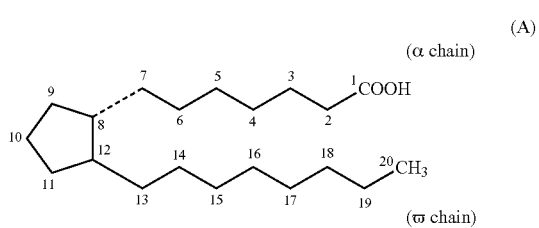 [SMILES: CCCCCCCCC1CCC[C@@H]1CCCCCCC(=O)O]

On the other hand, some of synthetic prostaglandin (PG) analogues have modified skeletons. The primary PGs are classified into PGAs, PGBs, PGCs, PGDs, PGEs, PGFs, PGGs, PGHs, PGIs and PGJs according to the structure of the five-membered ring moiety, and further classified into the following three types by the number and position of the unsaturated bond at the carbon chain moiety:

Subscript 1: 13,14-unsaturated-15-OH
Subscript 2: 5,6- and 13,14-diunsaturated-15-OH
Subscript 3: 5,6-, 13,14-, and 17,18-triunsaturated-15-OH.

Further, the PGFs are classified, according to the configuration of the hydroxyl group at the 9-position, into α type (the hydroxyl group is of an α-configuration) and β type (the hydroxyl group is of a β-configuration).

PGs are known to have various pharmacological and physiological activities, for example, vasodilatation, inducing of inflammation, platelet aggregation, stimulating uterine muscle, stimulating intestinal muscle, anti-ulcer effect and the like.

Prostones, having an oxo group at position 15 of prostanoic acid skeleton (15-keto type) and having a single bond between positions 13 and 14 and an oxo group at position 15 (13,14-dihydro-15-keto type), are fatty acid derivatives known as substances naturally produced by enzymatic actions during metabolism of the primary PGs and have some therapeutic effect. Prostones have been disclosed in U.S. Pat. Nos. 5,073,569, 5,534,547, 5,225,439, 5,166,174, 5,428,062, 5,380,709, 5,886,034, 6,265,440, 5,106,869, 5,221,763, 5,591,887, 5,770,759 and 5,739,161, the contents of these references are herein incorporated by reference.

Some fatty acid derivatives have been known as drugs used in the ophthalmic field, for example, for lowering intraocular pressure or treating glaucoma. For example, (+)-Isopropyl (Z)-7-[(1R,2R,3R,5S)-3,5-dihydroxy-2-[(3R)-3-hydroxy-5-phenylpentyl]cyclopentyl]-5-heptenoate (general name: latanoprost), Isopropyl(5Z)-7-((1R,2R,3R,5S)-3,5-dihydroxy-2-{(1E,3R)-3-hydroxy-4-[3-(trifluoromethyl)phenoxy]but-1-enyl}cyclopentyl)hept-5-enoate (general name: travoprost), (5Z)-7-{(1R,2R,3R,5S)-3,5-Dihydroxy-2-[(1E,3S)-3-hydroxy-5-phenylpent-1-en-1-yl]cyclopentyl}-N-ethylhept-5-enamide (general name: bimatoprost) and 1-Methylethyl(5Z)-7-{(1R,2R,3R,5S)-2-[(1E)-3,3-difluoro-4-phenoxy-1-butenyl]-3,5-dihydroxycyclopentyl}-5-heptenoate (general name: tafluprost) have been marketed as ophthalmic solution for the treatment of glaucoma and/or ocular hypertension under the name of Xalatan®, Travatan®, Lumigan® and Tapros®, respectively.

Some fatty acid derivatives have also been known as drugs used in systemic diseases for example, alprostadil ($PGE_1$), beraprost (prostacyclin analog), limaprost ($PGE_1$ derivative), misoprostol (PGE1 derivative), enprostil, dinoprost ($PGF_{2\alpha}$), gemeprost (PGE1 derivative) and epoprostenol (prostacyclin).

Further, prostones have also been known to be useful in the ophthalmic field, for example, for lowering intraocular pressure and treating glaucoma (see U.S. Pat. Nos. 5,001,153, 5,151,444, 5,166,178, 5,194,429 and 5,236,907), for treating cataract (see U.S. Pat. Nos. 5,212,324 and 5,686,487), for increasing the choroidal blood flow (see U.S. Pat. No. 5,221,690), for treating optic nerve disorder (see U.S. Pat. No. 5,773,471), the contents of these references are herein incorporated by reference. Ophthalmic solution comprising (+)-isopropyl (Z)-7-[(1R,2R,3R,5S)-3,5-dihydroxy-2-(3-oxodecyl)cyclopentyl]hept-5-enoate (general name: isopropyl unoprostone, or unoprostone ispropyl) has been marketed under the name of Rescula® as a pharmaceutical product for the treatment of glaucoma and ocular hypertension. Also, isopropyl unoprostone is known as a BK channel modulator. (Biochimica et Biophysica Acta 1768 (2007) 1083-1092). Documents cited in this paragraph are herein incorporated by reference.

DISCLOSURE OF THE INVENTION

The present invention relates to a novel fatty acid derivative-polymer conjugate. Especially, the present invention relates to a novel conjugate comprising a fatty acid derivative and an alkyl substituted polylactide compound.

In one aspect, the present invention relates to a pharmaceutical composition comprising a conjugate comprising a fatty acid derivative and an alkyl substituted polylactide compound.

DETAILED DESCRIPTION OF THE INVENTION

Figure 1:
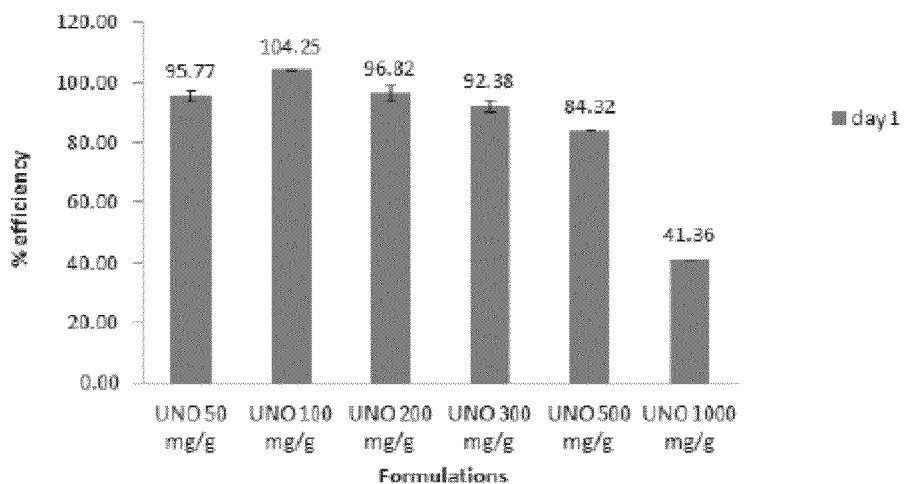
FIG. 1 shows efficiency of unoprostone isopropyl incorporation into MPEG-hexPLA polymer micelles.
Figure 2:
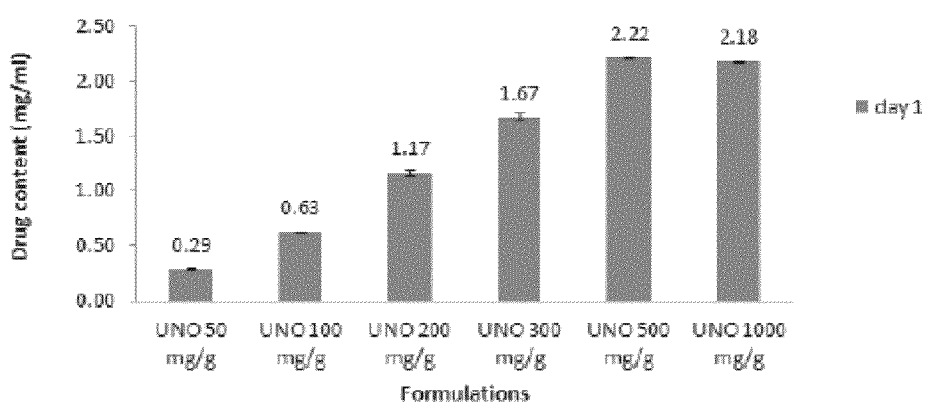
FIG. 2 shows actual obtained unoprostone isopropyl formulation concentrations for the given target concentrations.
Figure 3:
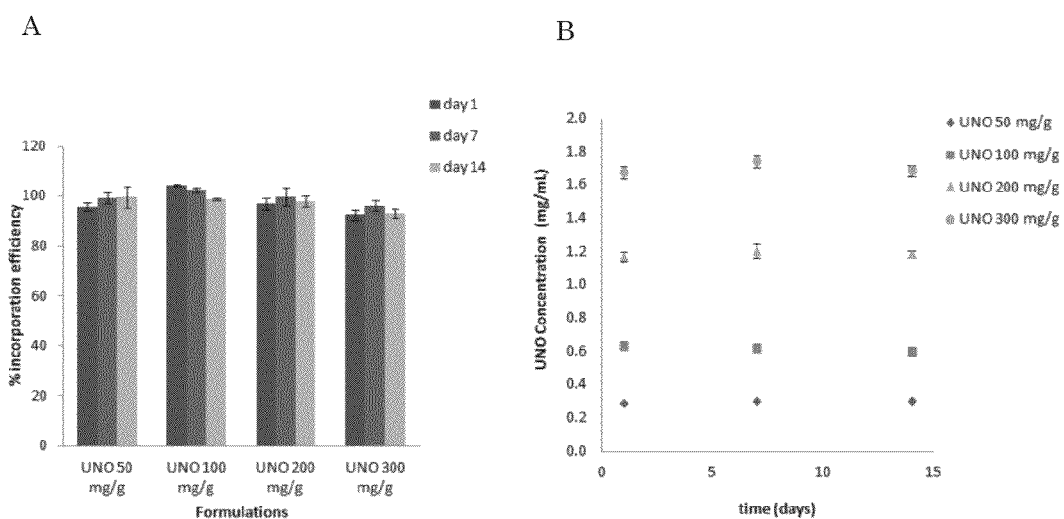
FIGS. 3 A and 3B show unoprostone isopropyl MPEG-hexPLA formulation stability at 4° C. over a period of two weeks.

The present invention relates to a novel conjugate comprising a fatty acid derivative and an alkyl substituted polylactide compound.

1) Conjugate

The term "conjugate" includes drug-polymer complex, drug-polymer combination, micelle formed by drug-polymer, or any other possible drug-polymer conjugate as long as the drug is incorporated, entrapped, dispersed or conjugated to the polymer matrix.

2) Fatty Acid Derivative

The nomenclature of the fatty acid derivative used herein is based on the numbering system of the prostanoic acid represented in the above formula (A).

The formula (A) shows a basic skeleton of the C-20 fatty acid derivative, but the present invention is not limited to those having the same number of carbon atoms. In the formula (A), the numbering of the carbon atoms which constitute the basic skeleton of the fatty acid derivatives starts at the carboxylic acid (numbered 1), and carbon atoms in the α-chain are numbered 2 to 7 towards the five-membered ring, those in the ring are 8 to 12, and those in the ω-chain are 13 to 20. When the number of carbon atoms is decreased in the α-chain, the number is deleted in the order starting from position 2; and when the number of carbon atoms is increased in the α-chain, compounds are named as substitution compounds having respective substituents at position 2 in place of carboxy group (C-1). Similarly, when the number of carbon atoms is decreased in the ω-chain, the number is deleted in the order starting from position 20; and when the number of carbon atoms is increased in the ω-chain, the carbon atoms at the position or later are named as a substituent at position 20. Stereochemistry of the compounds is the same as that of the above formula (A) unless otherwise specified.

In general, each of PGD, PGE and PGF represents a fatty acid derivative having hydroxy groups at positions 9 and/or 11, but in the present specification they also include those having substituents other than the hydroxy groups at positions 9 and/or 11. Such compounds are referred to as 9-deoxy-9-substituted-fatty acid derivatives or 11-deoxy-1'-substituted-fatty acid derivatives. A fatty acid derivative having hydrogen in place of the hydroxy group is simply named as 9- or 11-deoxy-fatty acid derivative.

As stated above, the nomenclature of a fatty acid derivative is based on the prostanoic acid skeleton. In the case the compound has similar partial structure as the primary PG, the abbreviation of "PG" may be used. Thus, a fatty acid derivative whose α-chain is extended by two carbon atoms, that is, having 9 carbon atoms in the α-chain is named as 2-decarboxy-2-(2-carboxyethyl)-PG compound. Similarly, a fatty acid derivative having 11 carbon atoms in the α-chain is named as 2-decarboxy-2-(4-carboxybutyl)-PG compound. Further, a fatty acid derivative whose ω-chain is extended by two carbon atoms, that is, having 10 carbon atoms in the ω-chain is named as 20-ethyl-PG compound. These compounds, however, may also be named according to the IUPAC nomenclatures.

Examples of the analogues including substitution compounds or derivatives of the above described fatty acid derivative include a fatty acid derivative whose carboxy group at the end of the alpha chain is esterified; a fatty acid derivative whose α chain is extended, a physiologically acceptable salt thereof, a fatty acid derivative having a double bond between positions 2 and 3 or a triple bond between positions 5 and 6; a fatty acid derivative having substituent(s) on carbon atom(s) at position(s) 3, 5, 6, 16, 17, 18, 19 and/or 20; and a fatty acid derivative having a lower alkyl or a hydroxy (lower) alkyl group at position 9 and/or 11 in place of the hydroxy group.

According to the present invention, preferred substituents on the carbon atom at position(s) 3, 17, 18 and/or 19 include alkyl having 1-4 carbon atoms, especially methyl and ethyl. Preferred substituents on the carbon atom at position 16 include lower alkyls such as methyl and ethyl, hydroxy, halogen atom such as chlorine and fluorine, and aryloxy such as trifluoromethylphenoxy. Preferred substituents on the carbon atom at position 17 include lower alkyl such as methyl and ethyl, hydroxy, halogen atom such as chlorine and fluorine, and aryloxy such as trifluoromethylphenoxy. Preferred substituents on the carbon atom at position 20 include saturated or unsaturated lower alkyl such as $C_{1-4}$ alkyl, lower alkoxy such as $C_{1-4}$ alkoxy, and lower alkoxy alkyl such as $C_{1-4}$ alkoxy-$C_{1-4}$ alkyl. Preferred substituents on the carbon atom at position 5 include halogen atoms such as chlorine and fluorine. Preferred substituents on the carbon atom at position 6 include an oxo group forming a carbonyl group. Stereochemistry of PGs having hydroxy, lower alkyl or hydroxy(lower)alkyl substituent on the carbon atom at positions 9 and 11 may be α, β or a mixture thereof.

Further, the above described analogues or derivatives may have a ω chain shorter than that of the primary PGs and a substituent such as alkoxy, cycloalkyl, cycloalkyloxy, phenoxy and phenyl at the end of the truncated ω-chain.

A fatty acid derivative used in the present invention is represented by the formula (I):

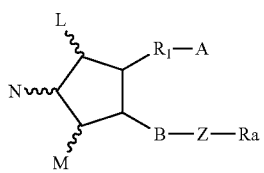
(I)

wherein L, M and N are hydrogen, hydroxy, halogen, lower alkyl, hydroxy(lower)alkyl, lower alkanoyloxy or oxo, wherein at least one of L and M is a group other than hydrogen, and the five-membered ring may have at least one double bond;

A is —CH$_3$, or —CH$_2$OH, —COCH$_2$OH, —COOH or a functional derivative thereof;

B is single bond, —CH$_2$—CH$_2$—, —CH=CH—, —C≡C—, —CH$_2$—CH$_2$—CH$_2$—, —CH=CH—CH$_2$—, —CH$_2$—CH=CH—, —C≡C—CH$_2$— or —CH$_2$—C≡C—;

Z is

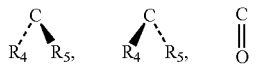

or single bond wherein R$_4$ and R$_5$ are hydrogen, hydroxy, halogen, lower alkyl, lower alkoxy or hydroxy(lower)alkyl, wherein R$_4$ and R$_5$ are not hydroxy and lower alkoxy at the same time;

R$_1$ is a saturated or unsaturated bivalent lower or medium aliphatic hydrocarbon residue, which is unsubstituted or substituted with halogen, lower alkyl, hydroxy, oxo, aryl or heterocyclic group, and at least one of carbon atom in the aliphatic hydrocarbon is optionally substituted by oxygen, nitrogen or sulfur; and Ra is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower)alkyloxy; aryl; aryloxy; heterocyclic group; heterocyclic-oxy group, and at least one of carbon atom in the aliphatic hydrocarbon is optionally substituted by oxygen, nitrogen or sulfur.

A preferred compound used in the present invention is represented by the formula (II):

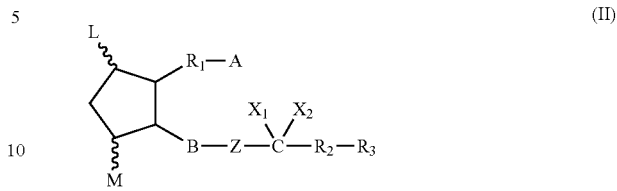
(II)

wherein L and M are hydrogen atom, hydroxy, halogen, lower alkyl, hydroxy(lower)alkyl, lower alkanoyloxy or oxo, wherein at least one of L and M is a group other than hydrogen, and the five-membered ring may have one or more double bonds;

A is —CH$_3$, or —CH$_2$OH, —COCH$_2$OH, —COOH or a functional derivative thereof;

B is single bond, —CH$_2$—CH$_2$—, —CH=CH—, —C≡C—, —CH$_2$—CH$_2$—CH$_2$—, —CH=CH—CH$_2$—, —CH$_2$—CH=CH—, —C≡C—CH$_2$— or —CH$_2$—C≡C—;

Z is

or single bond wherein R$_4$ and R$_5$ are hydrogen, hydroxy, halogen, lower alkyl, lower alkoxy or hydroxy(lower)alkyl, wherein R$_4$ and R$_5$ are not hydroxy and lower alkoxy at the same time;

X$_1$ and X$_2$ are hydrogen, lower alkyl, or halogen;

R$_1$ is a saturated or unsaturated bivalent lower or medium aliphatic hydrocarbon residue, which is unsubstituted or substituted with halogen, lower alkyl, hydroxy, oxo, aryl or heterocyclic group, and at least one of carbon atom in the aliphatic hydrocarbon is optionally substituted by oxygen, nitrogen or sulfur;

R$_2$ is a single bond or lower alkylene; and

R$_3$ is lower alkyl, lower alkoxy, lower alkanoyloxy, cyclo(lower)alkyl, cyclo(lower)alkyloxy, aryl, aryloxy, heterocyclic group or heterocyclic-oxy group, and at least one of carbon atom in the aliphatic hydrocarbon is optionally substituted by oxygen, nitrogen or sulfur.

In the above formula, the term "unsaturated" in the definitions for R$_1$ and Ra is intended to include at least one or more double bonds and/or triple bonds that are isolatedly, separately or serially present between carbon atoms of the main and/or side chains. According to the usual nomenclature, an unsaturated bond between two serial positions is represented by denoting the lower number of the two positions, and an unsaturated bond between two distal positions is represented by denoting both of the positions.

The term "lower or medium aliphatic hydrocarbon" refers to a straight or branched chain hydrocarbon group having 1 to 14 carbon atoms (for a side chain, 1 to 3 carbon atoms are preferable) and preferably 1 to 10, especially 1 to 8 carbon atoms.

The term "halogen atom" covers fluorine, chlorine, bromine and iodine.

The term "lower" throughout the specification is intended to include a group having 1 to 6 carbon atoms unless otherwise specified.

The term "lower alkyl" refers to a straight or branched chain saturated hydrocarbon group containing 1 to carbon atoms and includes, for example, methyl, ethyl, propyl, isopropyl, butyl, isobutyl, t-butyl, pentyl and hexyl.

The term "lower alkylene" refers to a straight or branched chain bivalent saturated hydrocarbon group containing 1 to 6 carbon atoms and includes, for example, methylene, ethylene, propylene, isopropylene, butylene, isobutylene, t-butylene, pentylene and hexylene.

The term "lower alkoxy" refers to a group of lower alkyl-O—, wherein lower alkyl is as defined above.

The term "hydroxy(lower)alkyl" refers to a lower alkyl as defined above which is substituted with at least one hydroxy group such as hydroxymethyl, 1-hydroxyethyl, 2-hydroxyethyl and 1-methyl-1-hydroxyethyl.

The term "lower alkanoyloxy" refers to a group represented by the formula RCO—O—, wherein RCO— is an acyl group formed by oxidation of a lower alkyl group as defined above, such as acetyl.

The term "cyclo(lower)alkyl" refers to a cyclic group formed by cyclization of a lower alkyl group as defined above but contains three or more carbon atoms, and includes, for example, cyclopropyl, cyclobutyl, cyclopentyl and cyclohexyl.

The term "cyclo(lower)alkyloxy" refers to the group of cyclo(lower)alkyl-O—, wherein cyclo(lower)alkyl is as defined above.

The term "aryl" may include unsubstituted or substituted aromatic hydrocarbon rings (preferably monocyclic groups), for example, phenyl, tolyl, xylyl. Examples of the substituents are halogen atom and halo(lower)alkyl, wherein halogen atom and lower alkyl are as defined above.

The term "aryloxy" refers to a group represented by the formula ArO—, wherein Ar is aryl as defined above.

The term "heterocyclic group" may include mono- to tri-cyclic, preferably monocyclic heterocyclic group which is 5 to 14, preferably 5 to 10 membered ring having optionally substituted carbon atom and 1 to 4, preferably 1 to 3 of 1 or 2 type of hetero atoms selected from nitrogen atom, oxygen atom and sulfur atom. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazinyl, pyrimidyl, pyrazinyl, 2-pyrrolinyl, pyrrolidinyl, 2-imidazolinyl, imidazolidinyl, 2-pyrazolinyl, pyrazolidinyl, piperidino, piperazinyl, morpholino, indolyl, benzothienyl, quinolyl, isoquinolyl, purinyl, quinazolinyl, carbazolyl, acridinyl, phenanthridinyl, benzimidazolyl, benzimidazolinyl, benzothiazolyl, phenothiazinyl. Examples of the substituent in this case include halogen, and halogen substituted lower alkyl group, wherein halogen atom and lower alkyl group are as described above.

The term "heterocyclic-oxy group" means a group represented by the formula HcO—, wherein Hc is a heterocyclic group as described above.

The term "functional derivative" of A includes salts (preferably pharmaceutically acceptable salts), ethers, esters and amides.

Suitable "pharmaceutically acceptable salts" include conventionally used non-toxic salts, for example a salt with an inorganic base such as an alkali metal salt (such as sodium salt and potassium salt), an alkaline earth metal salt (such as calcium salt and magnesium salt), an ammonium salt; or a salt with an organic base, for example, an amine salt (such as methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino)ethane salt, monomethyl-monoethanolamine salt, procaine salt and caffeine salt), a basic amino acid salt (such as arginine salt and lysine salt), tetraalkyl ammonium salt and the like. These salts may be prepared by a conventional process, for example from the corresponding acid and base or by salt interchange.

Examples of the ethers include alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower)alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, t-butyl ester, pentyl ester and 1-cyclopropylethyl ester; lower alkenyl esters such as vinyl ester and allyl ester; lower alkynyl esters such as ethynyl ester and propynyl ester; hydroxy(lower) alkyl ester such as hydroxyethyl ester; lower alkoxy (lower) alkyl esters such as methoxymethyl ester and 1-methoxyethyl ester; and optionally substituted aryl esters such as, for example, phenyl ester, tolyl ester, t-butylphenyl ester, salicyl ester, 3,4-di-methoxyphenyl ester and benzamidophenyl ester; and aryl(lower)alkyl ester such as benzyl ester, trityl ester and benzhydryl ester.

The amide of A mean a group represented by the formula —CONR'R", wherein each of R' and R" is hydrogen, lower alkyl, aryl, alkyl- or aryl-sulfonyl, lower alkenyl and lower alkynyl, and include for example lower alkyl amides such as methylamide, ethylamide, dimethylamide and diethylamide; arylamides such as anilide and toluidide; and alkyl- or aryl-sulfonylamides such as methylsulfonylamide, ethylsulfonylamide and tolylsulfonylamide.

Preferred examples of L and M include hydrogen, hydroxy and oxo, and especially, L and M are both hydroxy, or L is oxo and M is hydrogen or hydroxy.

Preferred example of A is —COOH, its pharmaceutically acceptable salt, ester or amide thereof.

Preferred example of $X_1$ and $X_2$ are both being halogen atoms, and more preferably, fluorine atoms, so called 16,16-difluoro type.

Preferred $R_1$ is a hydrocarbon residue containing 1-10 carbon atoms, preferably 6-10 carbon atoms. Further, at least one carbon atom in the aliphatic hydrocarbon is optionally substituted by oxygen, nitrogen or sulfur. Examples of $R_1$ include, for example, the following groups

—CH$_2$—CH$_2$—CH$_2$—CH$_2$—CH$_2$—CH$_2$—,

—CH$_2$—CH=CH—CH$_2$—CH$_2$—CH$_2$—,

—CH$_2$—CH$_2$—CH$_2$—CH$_2$—CH=CH—,

—CH$_2$—C≡C—CH$_2$—CH$_2$—CH$_2$—,

—CH$_2$—CH$_2$—CH$_2$—CH$_2$—O—CH$_2$—,

—CH$_2$—CH=CH—CH$_2$—O—CH$_2$—,

—CH₂—C≡C—CH₂—O—CH₂—,

—CH₂—CH₂—CH₂—CH₂—CH₂—CH₂—CH₂—,

—CH₂—CH=CH—CH₂—CH₂—CH₂—CH₂—,

—CH₂—CH₂—CH₂—CH₂—CH₂—CH=CH—,

—CH₂—C≡C—CH₂—CH₂—CH₂—CH₂—,

—CH₂—CH₂—CH₂—CH₂—CH₂—CH(CH₃)—CH₂—,

—CH₂—CH₂—CH₂—CH₂—CH(CH₃)—CH₂—,

—CH₂—CH₂—CH₂—CH₂—CH₂—CH₂—CH₂—CH₂—,

—CH₂—CH=CH—CH₂—CH₂—CH₂—CH₂—CH₂—,

—CH₂—CH₂—CH₂—CH₂—CH₂—CH₂—CH=CH—,

—CH₂—C≡C—CH₂—CH₂—CH₂—CH₂—CH₂—, and

—CH₂—CH₂—CH₂—CH₂—CH₂—CH₂—CH(CH₃)—CH₂—,

Preferred Ra is a hydrocarbon containing 1-10 carbon atoms, more preferably, 1-8 carbon atoms. Ra may have one or two side chains having one carbon atom. Further, at least one carbon atom in the aliphatic hydrocarbon is optionally substituted by oxygen, nitrogen or sulfur.

Preferable compounds include Ra is substituted by halogen and/or Z is C=O in the formula (I), or one of X1 and X2 is substituted by halogen and/or Z is C=O in the formula (II).

Example of the preferred embodiment is a (+)-isopropyl (Z)-7-[(1R,2R,3R,5S)-3,5-dihydroxy-2-(3-oxodecyl)cyclopentyl]hept-5-enoate (general name: isopropyl unoprostone, or unoprostone ispropyl), (−)-7-[(2R,4aR,5R,7aR)-2-(1,1-difluoropentyl)-2-hydroxy-6-oxooctahydrocyclopenta[b]pyran-5-yl]heptanoic acid (lubiprostone), (−)-7-{(2R,4aR,5R,7aR)-2-[(3S)-1,1-difluoro-3-methylpentyl]-2-hydroxy-6-oxooctahydrocyclopenta[b]pyran-5-yl}heptanoic acid (cobiprostone) and (−)-7-[(1R,2R)-2-(4,4-difluoro-3-oxooctyl)-5-oxocyclopentyl]heptanoic acid, its tautomeric isomers or its functional derivative thereof.

The configuration of the ring and the α- and/or ω chains in the above formula (I) and (II) may be the same as or different from that of the primary PGs. However, the present invention also includes a mixture of a compound having a primary type configuration and a compound of a non-primary type configuration.

In the present invention, the fatty acid derivative which is dihydro between 13 and 14, and keto(=O) at 15 position may be in the keto-hemiacetal equilibrium by formation of a hemiacetal between hydroxy at position 11 and keto at position 15.

For example, it has been revealed that when both of X₁ and X₂ are halogen atoms, especially, fluorine atoms, the compound contains a tautomeric isomer, bicyclic compound.

If such tautomeric isomers as above are present, the proportion of both tautomeric isomers varies with the structure of the rest of the molecule or the kind of the substituent present. Sometimes one isomer may predominantly be present in comparison with the other. However, it is to be appreciated that the present invention includes both isomers.

Further, the fatty acid derivatives used in the invention include the bicyclic compound and analogs or derivatives thereof.

The bicyclic compound is represented by the formula (III)

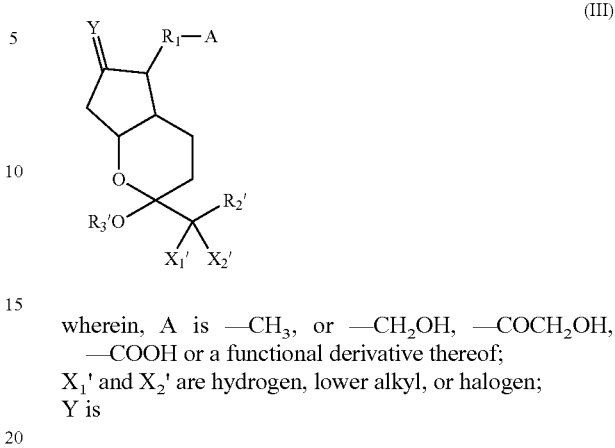

(III)

wherein, A is —CH₃, or —CH₂OH, —COCH₂OH, —COOH or a functional derivative thereof;
X₁' and X₂' are hydrogen, lower alkyl, or halogen;
Y is

wherein R₄' and R₅' are hydrogen, hydroxy, halogen, lower alkyl, lower alkoxy or hydroxy(lower)alkyl, wherein R₄' and R₅' are not hydroxy and lower alkoxy at the same time.

R₁ is a saturated or unsaturated divalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur; and R₂' is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower)alkyloxy; aryl; aryloxy; heterocyclic group; heterocyclic-oxy group, and at least one of carbon atom in the aliphatic hydrocarbon is optionally substituted by oxygen, nitrogen or sulfur.

R₃' is hydrogen, lower alkyl, cyclo(lower)alkyl, aryl or heterocyclic group.

Furthermore, while the compounds used in the invention may be represented by a formula or name based on keto-type regardless of the presence or absence of the isomers, it is to be noted that such structure or name does not intend to exclude the hemiacetal type compound.

In the present invention, any of isomers such as the individual tautomeric isomers, the mixture thereof, or optical isomers, the mixture thereof, a racemic mixture, and other steric isomers may be used in the same purpose.

Some of the compounds used in the present invention may be prepared by the method disclosed in U.S. Pat. Nos. 5,073,569, 5,166,174, 5,221,763, 5,212,324, 5,739,161 and 6,242,485 (these cited references are herein incorporated by reference).

Another preferred embodiment of the present invention includes some fatty acid derivatives known as drugs used in the ophthalmic field, for example, (+)-Isopropyl(Z)-7-[(1R,2R,3R,5S)-3,5-dihydroxy-2-[(3R)-3-hydroxy-5-phenylpentyl]cyclopentyl]-5-heptenoate (general name: latanoprost), Isopropyl(5Z)-7-((1R,2R,3R,5S)-3,5-dihydroxy-2-{(1E,3R)-3-hydroxy-4-[3-(trifluoromethyl)phenoxy]but-1-enyl}cyclopentyl)hept-5-enoate (general name: travoprost), (5Z)-7-{(1R,2R,3R,5S)-3,5-Dihydroxy-2-[(1E,3S)-3-hydroxy-5-phenylpent-1-en-1-yl]cyclopentyl}-N-ethylhept-5-enamide (general name: bimatoprost) and 1-Methylethyl (5Z)-7-{(1R,2R,3R,5S)-2-[(1E)-3,3-difluoro-4-phenoxy-1-butenyl]-3,5-dihydroxy cyclopentyl}-5-heptenoate (general name: tafluprost) have been marketed as ophthalmic solution for the treatment of glaucoma and/or ocular hypertension under the name of Xalatan®, Travatan®, Lumigan® and Tapros®, respectively.

Further another preferred embodiment of the present invention includes some fatty acid derivatives known as drugs used in systemic diseases for example, alprostadil ($PGE_1$), beraprost (prostacyclin analog), limaprost ($PGE_1$ derivative), misoprostol (PGE1 derivative), enprostil, dinoprost ($PGF_{2\alpha}$), gemeprost (PGE1 derivative) and epoprostenol (prostacyclin).

3) Alkyl Substituted Polylactide Compound

"Alkyl substituted polylactide", as used herein, refers to a compound structure:

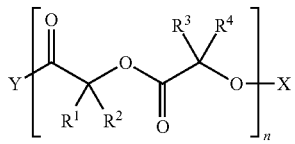

wherein $R^1$, $R^2$, $R^3$, and $R^4$ are each independently chosen from the group consisting of alkyl (e.g., unsubstituted alkyl), H, alkenyl and alkylaryl (e.g., unsubstituted alkylaryl); wherein X is hydrogen or, alternatively, has been produced as a result of any further functionalization by chemical reaction on the —OH group formed by the —OX wherein X is hydrogen; Y been derived from any initiator alcohol, or Y is selected from the group consisting of —OH, an alkoxy, benzyloxy and —O—($CH_2$—$CH_2$—O)$_p$—$CH_3$; and wherein p is 1 to 700, more preferably 1 to 250; and wherein n is an integer from 1 to 500, more preferably 1 to 100, more preferably 1 to 50, more preferably 1 to 25. In certain embodiments, n is from 1 to 12, from 1 to 6, 1, 2, 3, 4, 5, 6, 7, 8, 9, or 10.

In certain embodiments, $R^4$ and $R^3$ are hydrogen and $R^2$ and $R^4$ are lower alkyl. For example, $R^2$ and $R^4$ may be —($CH_2$)$_m$—$CH_3$, wherein m is from 0 to 20, more preferably 0 to 15, more preferably 0 to 10, more preferably m=0 or m=5. In certain embodiments, m is from 0 to 6, 0, 1, 2, 3, 4, 5, 6, 7, 8, 9, 10, 11 or 12.

In certain embodiments an alkyl substituted polylactide may have the following structure:

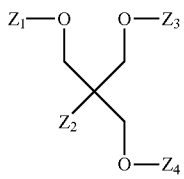

wherein $Z_2$ is selected from the group consisting of —$CH_3$ and —$CH_2$—O—$Z_5$; and wherein $Z_1$, $Z_3$, $Z_4$, and $Z_5$, each independently has the structure:

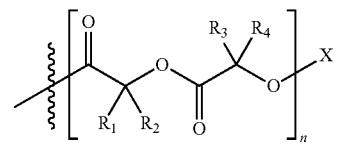

wherein $R_1$, $R_2$, $R_3$, and $R_4$ are each independently chosen from the group consisting of alkyl (e.g., unsubstituted alkyl), H, alkenyl and alkylaryl (e.g., unsubstituted alkylaryl); wherein n is 1 to 100; wherein X is hydrogen, —C(O)—CH=$CH_2$ or any other functional or crosslinking group. In certain embodiments, n is 1 to 75, more preferably 1 to 50, more preferably 1 to 25. In certain embodiments, $R_1$ and $R_3$ are hydrogen; and $R_2$ and $R_4$ are lower alkyl. In certain embodiments, $R_2$ and $R_4$ are —($CH_2$)$_m$—$CH_3$, wherein m is from 0 to 20. In certain embodiments, m is from 0 to 20, more preferably 0 to 15, more preferably 0 to 10, more preferably m=0 or m=5. In certain embodiments, $Z_2$ is —$CH_3$; $R_1$ and $R_3$ are hydrogen; $R_2$ and $R_4$ are —($CH_2$)$_m$—$CH_3$, wherein m is from 0 to 20; and X is hydrogen. In certain embodiments, $Z_2$ is —$CH_3$; $R_1$ and $R_3$ are hydrogen; $R_2$ and $R_4$ are —($CH_2$)$_m$—$CH_3$, wherein m is from 0 to 20; and X is —C(O)—CH=$CH_2$ or any other functional or crosslinking group. In certain embodiments, $Z_2$ is —$CH_2$—O—$Z_5$; $R_1$ and $R_3$ are hydrogen; $R_2$ and $R_4$ are —($CH_2$)$_m$—$CH_3$, wherein m is from 0 to 20; and X is hydrogen. In certain embodiments, $Z_2$ is —$CH_2$—O—$Z_5$; $R_1$ and $R_3$ are hydrogen; $R_2$ and $R_4$ are —($CH_2$)$_m$—$CH_3$, wherein m is from 0 to 20; and X is —C(O)—CH=$CH_2$. In certain embodiments, m may be from 0 to 20, 0 to 16, 0 to 12, or 0 to 6.

In certain embodiments an alkyl substituted polylactide may have the structure:

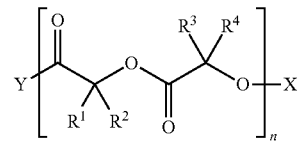

wherein $R^1$, $R^2$, $R^3$, and $R^4$ are each independently chosen from the group consisting of alkyl (e.g., unsubstituted alkyl), H, alkenyl and alkylaryl (e.g., unsubstituted alkylaryl); wherein n is 1 to 100; wherein X is hydrogen or —C(O)—CH=$CH_2$ or any other functional or crosslinking group; and Y is —O—($CH_2$—$CH_2$—O)$_p$—$CH_3$; wherein p is 1 to 700, more preferably 1 to 250. In certain embodiments, n is 1 to 100, more preferably 1 to 75, more preferably 1 to 50, more preferably 1 to 25, 1 to 12 or 1 to 6. In certain embodiments, $R^4$ and $R^3$ are hydrogen; and $R^2$ and R3 are lower alkyl. In certain embodiments, $R^2$ and $R^4$ are —($CH_2$)$_m$—$CH_3$, wherein m is from 0 to 20, more preferably 0 to 6. In certain embodiments, m is from 0 to 6, 0, 1, 2, 3, 4, 5, 6, 7, 8, 9, 10, 11, 12.

Alkyl substituted polylactides of the present invention may be synthesized according to the description of WO2007/012979 or WO2012/014011.

As used herein the specification, "a" or "an" may mean one or more. As used herein in the claim(s), when used in conjunction with the word "comprising", the words "a" or "an"

may mean one or more than one. As used herein "another" may mean at least a second or more.

It is contemplated that any embodiment discussed in this specification can be implemented with respect to any method or composition of the invention, and vice versa. Furthermore, compositions of the invention can be used to achieve the methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

An "alkyl" group, as used herein to describe a polylactide, refers to a saturated aliphatic hydrocarbon, including straight-chain, branched chain, and cyclic alkyl groups. Preferably, the alkyl group has 1 to 20 carbons, more preferably 1 to 12 carbons, more preferably 1 to 10. Most preferably, it is a lower alkyl of from 1 to 12 carbons. The alkyl groups of the present invention are preferably unsubstituted. For example, —$CH_3$, —$CH(CH_3)_2$ and —$(CH_2)_nCH_3$, wherein n is 1, 2, 3, 4, 5, 6, 7, 8, 9, 10, 11, 12, 13, 14, 15, 16, 17, 18, 19 or 20 are contemplated alkyl groups that may be used in certain embodiments of the present invention.

An "alkenyl" group, as used herein to describe a polylactide, refers to an unsaturated aliphatic hydrocarbon, including straight-chain, branched chain, and cyclic alkyl groups. Preferably, the alkenyl group has 1 to 20 carbons, more preferably 1 to 12 carbons, more preferably 1 to 10. Most preferably, it is a lower alkenyl of from 1 to 12 carbons.

An "aryl" group, as used herein to describe a polylactide, refers to an unsubstituted aromatic group which has at least one ring having a conjugated pi electron system, and includes carbo cyclic aryl, heterocyclic aryl, and biaryl groups. In certain preferred embodiments, the aryl is an unsubstituted phenyl.

An "alkylaryl" group, as used herein to describe a polylactide, refers to an alkyl (as described above), co valently joined to an aryl group (as described above). Preferably, the alkyl is a lower alkyl. For example, —$(CH_2)H(C_6H_5)$ is contemplated as an alkylaryl, wherein n is 1 to 20.

An "alkoxy" group, as used herein to describe a polylactide, refers to an "–O-alkyl" group, where "alkyl" is defined above.

A "benzyloxy" group, as used herein to describe a polylactide, refers to the group

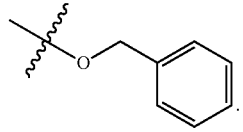 [SMILES: *OCc1ccccc1]

"Viscous", as used herein to describe a polylactide, refers to a polylactide that has a glass transition temperature (Tg) value of less than 44° C. (degree Celsius), more preferably less than 36° C., more preferably less than ° C., more preferably less than 34° C., more preferably less than 33° C., more preferably less than 32° C., more preferably less than 31° C., more preferably less than 30° C., more preferably less than 29° C., more preferably less than 28° C., more preferably less than 27° C., more preferably less than 26° C., more preferably less than 25° C., more preferably less than 24° C., more preferably less than 23° C., more preferably less than 22° C., more preferably less than 21° C., more preferably less than 20° C., more preferably less than 19° C., more preferably less than 18° C., more preferably less than 17° C., more preferably less than 16° C., more preferably less than 15° C., more preferably less than ° C., more preferably less than 13° C., more preferably less than 12° C., more preferably less than 11° C., more preferably less than 10° C., more preferably less than 9° C., more preferably less than 8° C., more preferably less than 7° C., more preferably less than 6° C., more preferably less than 5° C., more preferably less than 4° C., more preferably less than 3° C., more preferably less than 2° C., more preferably less than 1° C., more preferably less than 0° C., more preferably less than −1° C., more preferably less than −2° C., more preferably less than −3° C., more preferably less than −4° C., more preferably less than −5° C., more preferably less than −6° C., more preferably less than −7° C., more preferably less than −8° C., more preferably less than −9° C., most preferably less than −10° C.

The polylactides of the present invention may be used in combination with other polylactides, polyglycolides and their copolymers. For example, the polylactides of the present invention may be admixed with or contacted with a second compound and the resulting composition may be used for drug delivery. Compounds which may be used as the second compound or in combination with the polylactides of the present invention include polyglycolide (PLGA), polylactic acid (PLA), polycaprolactone (PCL), polyethylene glycol (PEG), polydioxanone (PDO), poly(D,L-lactide-co-glycolide) and poly(L-lactide-co-glycolide), poly(hydroxyl alkanoate) (PHA), and biodegradable and biocompatible polymers. Biocompatible polymers include polyester, polyether, polyanhydride, polyamines, poly(ethylene imines) polyamides, polyesteramides, polyorthoesters, polydioxanones, polyacetals, polyketals, polycarbonates, polyphosphoesters, polybutylene, polyterephthalate, polyorthocarbonates, polyphosphazenes, polyurethanes, polytetrafluorethylenes (PTFE), polysuccinates, poly(malic acid), poly(amino acids), polyvinylpyrrolidone, polyhydroxycellulose, polysaccharides, chitin, chitosan, hyaluronic acid, and copolymers, terpolymers and mixtures thereof. In certain embodiments, synthetic polymers and/or natural polymers may be used as the second compound or in combination with polylactides of the present invention. Details are referred in WO2007/012979.

In certain embodiments it may be desirable to contact or admix an alkyl substituted polylactide with one or more plasticizers, in order to alter the physical properties (e.g., lowering the Tg) of the resulting composition. Plasticizers which may be used in combination with an alkyl substituted polylactide include all FDA approved plasticizers, such as benzyl benzoates, cellulose acetates, cellulose acetate phthalates, chlorobutanol, dextrines, dibutyl sebacate, dimethyl sebacate, acetyl phthalates, diethyl phthalate, dibutyl phthalate, dipropyl phthalate, dimethyl phthalate, dioctyl phthalate, methyl cellulose, ethyl cellulose, hydroxylethyl cellulose, hydroxypropyl cellulose, hydroxypropyl methyl celluloses, gelatine, glycerines, glyceryl monostearate, monoglycerides, mono and di-acetylated monoglycerides, glycerol, mannitol, mineral oils and lanolin alcohols, petrolatum and lanolin alcohols, castor oil, vegetable oils, coconut oil, polyethylene glycol, polymethacrylates and copolymers thereof, polyvinyl-pyrrolidone, propylene carbonates, propylene glycol, sorbitol, suppository bases, diacetin, triacetin, triethanolamine, esters of citric acid, triethyl citrate, acetyl triethyl citrate, acetyl tributyl citrate, triethyl citrate, esters of phosphoric acid.

For example, certain alkyl substituted polylactides of the present invention (e.g., polylactides with higher molecular weights) may be waxy and thus not injectable. However, these alkyl substituted polylactides may still retain the very desirable property of being very hydrophobic in comparison to normal PLA/PLGA, thus having an advantage for many pharmaceutical applications. An increased hydrophobic drug incorporation into the alkyl substituted polylactide due to the increased hydrophobicity of the polylactide. Certain alkyl substituted polylactides of the present invention (e.g., polylactides with higher molecular weights) may exhibit better control of drug release. Thus, in certain embodiments a non-injectable alkyl substituted polylactide could be made injectable by admixing a plasticizer with the polylactide.

4) Pharmaceutical Preparations

Pharmaceutical compositions of the present invention comprise a conjugate comprising a fatty acid derivative and an alkyl substituted polylactide compound. Further it is recognized that one or more alkyl substituted polylactide may be used in combination with an additional agent in or as a pharmaceutically acceptable carrier.

The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one alkyl substituted polylactide or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The alkyl substituted polylactide may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The alkyl substituted polylactide may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens {e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include alkyl substituted polylactide, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the, art as lipids are also encompassed by the compositions and methods of the present invention.

One of ordinary skill in the art would be familiar with the range of techniques that can be employed for dispersing a composition in a lipid vehicle. For example, the alkyl substituted polylactide may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

A. Ophthalmic Compositions and Formulations

In preferred embodiments of the present invention, the conjugates are formulated to be administered topically to the eyes of the patient. The ophthalmic composition of the present invention includes any dosage form for ocular topical administration used in the field of ophthalmology, such as an ophthalmic solution, an eye drop and an eye ointment. The ophthalmic composition can be prepared in accordance with conventional means known in the relevant technical field.

The ophthalmic solution or eye drop is prepared by dissolving an active ingredient in a solvent such as an aqueous sterilization solution (for example, brine and buffer solution), or mixing with a powder composition which is dissolved at the time of use. The eye ointment is prepared by mixing an active ingredient with a base.

An "osmotic agent" may added to the ophthalmic composition. The osmotic agent or equivalently an osmoregulating chemical may be any one used usually in the ophthalmology field. Examples of the osmoregulating chemical include, but are not limited to, sodium chloride, potassium chloride, calcium chloride, sodium hydrogen carbonate, sodium carbonate, magnesium sulfate, sodium hydrogen phosphate, sodium dihydrogen phosphate, potassium dihydrogen phosphate, boric acid, borax, sodium hydroxide, hydrochloric acid, mannitol, sorbitol, glucose, glycerin, propylene glycol, polyethylene glycol and the like. The osmoregulating chemical is preferably a sugar alcohol such as mannitol or sorbitol and/or a polyol such as glycerin or propylene glycol.

In the present invention, in order to improve solubility of the fatty acid derivative in the solvent, a solubilizing agent such as a surfactant can be used. The surfactant used in the present invention is not limited as long as it can achieve the object, and a nonionic surfactant is preferred. Examples of the nonionic surfactant include polyoxyethylene sorbitan fatty acid esters such as polyoxyethylene sorbitan monooleate (Polysorbate 80), polyoxyethylene sorbitan monostearate (Polysorbate 60), polyoxyethylene sorbitan monopalmitate (Polysorbate 40), polyoxyethylene sorbitan monolaurate, polyoxyethylene sorbitan trioleate and polyoxyethylene sorbitan tristearate (Polysorbate 65); polyoxyethylene hardened castor oils such as polyoxyethylene hardened castor oil 10, polyoxyethylene hardened castor oil 40, polyoxyethylene hardened castor oil 50 and polyoxyethylene hardened castor oil 60; polyoxyethylene polyoxypropylene glycols such as polyoxyethylene (160) polyoxypropylene (30) glycol [Pluronic F68] and polyoxyethylene (42) polyoxypropylene (67)

glycol [Pluronic P123]; polyoxyethylene fatty acid esters such as polyoxyethylene 40 monostearate; and polyoxyethylene alkyl ethers such as polyoxy 10 oleyl ether (Brij 97) and polyoxyl 20 oleyl ether (Brij 98). Preferably, polyoxyethylene sorbitan monooleate (Polysorbate 80), polyoxyethylene hardened castor oil 60, polyoxyethylene 40 monostearate, polyoxyl 10 oleyl ether and the like are exemplified, and these nonionic surfactants may be used alone, or two or more kinds of them may be used in combination.

Furthermore, an additive used usually in the field of ophthalmology may be optionally added to the composition of the present invention. Examples of the additive include buffers (for example, boric acid, borax, sodium hydrogen phosphate and sodium dehydrogen phosphate, sodium edetate), preservatives (for example, benzalkonium chloride, benzethonium chloride and chlorobutanol), thickeners (for example, polysaccharides such as sodium hyaluronate, chondroitin sulfate, guar gum, gellan gum, xanthan gum and sodium alginate; cellulose polymers such as methyl cellulose, methyl ethyl cellulose and hydroxypropyl methyl cellulose; sodium polyacrylate, a carboxyvinyl polymer and a crosslinked polyacrylic acid.

In the preparation of the eye ointment, the composition may contain, in addition to the above additives, commonly used eye ointment bases. Examples of the eye ointment bases include, but are not limited to, oily bases such as petrolatum, liquid paraffin, polyethylene, Selene 50, Plastibase, macrogol or a combination thereof; emulsion bases containing an oil phase and an aqueous phase emulsified by the surfactant; and water-soluble bases such as hydroxypropyl methyl cellulose, carboxypropyl methyl cellulose and polyethylene glycol.

The term "dosage unit form" and "dosage form" as used herein refer to a single entity for drug administration. In one embodiment, the composition of the present invention may be formulated as a sterile unit dose containing no preservative or substantially free of preservative. The unit dosage form may be administered at one, two, three, four, or more times per day. When ocular local administration is used, one, two, three, four, or more drops may be administered at each time. In one embodiment, the ophthalmic solution is administered at least three drops per day. In another embodiment, the ophthalmic solution is administered at least four drops per day. In another embodiment, the ophthalmic solution is administered at least two drops per time, twice a day. In yet another embodiment, the ophthalmic solution is administered at least two drops per time with at least a five minute interval between drops, twice a day.

In one embodiment, the composition is administered by injection, ophthalmic pump, by means of a contact lens, a cellulose lens, a micropump, a conjunctival pump, an implantable device, a gel capsule, a patch, etc.

The concentration of the fatty acid derivative used in the present invention varies depending on the compounds used, kinds of subjects, age, body weight, symptoms to be treated, desired therapeutic effect, dose, treatment duration and the like, and appropriately proper concentration can be selected.

As used herein, "ocular locally administering" includes administration via eye drop, periocular (e.g., subTenon's), subconjunctival, intraocular, subretinal, suprachoroidal and retrobulbar administrations. Ocular local administration may also be administered topically using, for example, an ophthalmic ointment, a gel, a patch, injection, or by means of a contact lens, a cellulose lens, an ophthalmic pump, a micropump, a conjunctival pump, an injector, or an implantable device.

In the present invention, in the case of using isopropyl unoprostone, the concentration of the compound is 0.12 w/v % or more, and preferably 0.15 w/v % or more. The upper limit of the concentration is not particularly restrictive and may be set at approximately 10 w/v %.

B. Alimentary Compositions and Formulations

In preferred embodiments of the present invention, the alkyl substituted polylactide are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al, 1997; Hwang et al, 1998; U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

C. Parenteral Compositions and Formulations

In further embodiments, an alkyl substituted polylactide may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,753,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

D. Miscellaneous Pharmaceutical Compositions and Formulations

In other preferred embodiments of the invention, the active compound alkyl substituted polylactide may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays have been described, e.g., in U.S. Pat. Nos. 5,756,353 and 5,804,212 (each specifically incorporated herein by reference in its entirety). Likewise, the delivery of drugs using intranasal microparticle resins (Takenaga et al, 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroethey-lene support matrix is described in U.S. Pat. No. 5,780,045 (specifically incorporated herein by reference in its entirety). The term aerosol refers to a colloidal system of finely divided solid or liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE

1 Introduction

Objective is the evaluation of the methoxypoly(ethylene glycol)-hexyl-substituted poly(lactic acid) [MPEG-hexPLA] polymer micelles' potential to incorporate and solubilize unoprostone isopropyl.

2 Studies

The incorporation studies were carried out by a standard formulation protocol. Briefly, a defined amount of the provided unoprostone isopropyl ethanol solution was taken and the ethanol rapidly evaporated, the remaining compound was re-dissolved together with the MPEG-hexPLA excipient in acetone and added dropwise under sonication into water, followed by evaporation of the organic solvent and equilibration of the micelle solution overnight.

The results of the incorporation studies with increasing targeted drug loadings are summarized in the following FIGS. 1 and 2. As it can be seen, for loadings up to 500 mg unoprostone isopropyl per gram MPEGhexPLA, loading efficiencies higher than 80% could be obtained by this simple procedure (FIG. 1), corresponding to 2.22 mg drug per mL formulation (FIG. 2). Incorporation efficiencies higher 90% were obtained for loadings up to 300 mg/g, corresponding to concentrations up 1.67 mg/mL. The latter formulations with a minimum of drug loss in the formulation procedure gave transparent formulations.

3 Observations

Storing these formulations at 4° C. showed so far an excellent formulation stability with no drug loss from the micelles (FIG. 3).

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A conjugate comprising a fatty acid derivative and an alkyl substituted polylactide compound, wherein the fatty acid derivative is represented by the formula (I):

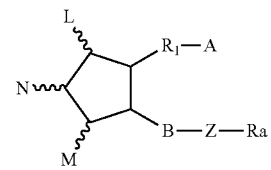

(I)

wherein L, M and N are hydrogen, hydroxy, halogen, straight or branched C1-6 alkyl, hydroxy(straight or branched C1-6)alkyl, straight or branched C1-6 alkanoyloxy or oxo, wherein at least one of L and M is a group other than hydrogen, and the double bond in the five-membered ring is optional;

A is $-CH_3$, or $-CH-_2OH$, $-COCH_2OH$, $-COOH$ or a functional derivative thereof;

B is single bond, $-CH_2-CH_2-$, $-CH{=}CH-$, $-C{\equiv}C-$, $-CH_2-CH_2-CH_2-$, $-CH{=}CH-CH_2-$, $-CH_2-CH{=}CH-$, $-C{\equiv}C-CH_2-$ or $-CH_2-C{\equiv}C-$;

Z is 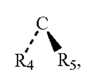 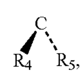 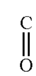 or single bond wherein $R_4$ and $R_5$ are hydrogen, hydroxy, halogen, straight or branched C1-6 alkyl, straight or branched C1-6 alkoxy or hydroxy(straight or branched C1-6) alkyl, wherein $R_4$ and $R_5$ are not hydroxy and straight or branched C1-6 alkoxy at the same time;

$R_1$ is a saturated or unsaturated bivalent straight or branched C1-14 aliphatic hydrocarbon residue, which is unsubstituted or substituted with halogen, straight or branched C1-6 alkyl, hydroxy, oxo, aryl or heterocyclic group, and at least one of carbon atom in the aliphatic hydrocarbon is optionally substituted by oxygen, nitrogen or sulfur;

Ra is a saturated or unsaturated straight or branched C1-14 aliphatic hydrocarbon residue, which is unsubstituted or substituted with halogen, oxo, hydroxy, straight or branched C1-6 alkyl, straight or branched C1-6 alkoxy, straight or branched C1-6 alkanoyloxy, cyclo(straight or branched C3-6)alkyl, cyclo(straight or branched C3-6) alkyloxy, aryl, aryloxy, heterocyclic group or heterocyclic-oxy group; straight or branched C1-6 alkoxy; straight or branched C1-6 alkanoyloxy; cyclo(straight or branched C3-6)alkyl; cyclo(straight or branched C3-6) alkyloxy; aryl; aryloxy; heterocyclic group; heterocyclic-oxy group, and at least one of carbon atom in the aliphatic hydrocarbon is optionally substituted by oxygen, nitrogen or sulfur; and provided that Z is $C{=}O$ and/or B is $-CH_2-CH_2-$.

2. The conjugate of claim 1, wherein Z is C=O.

3. The conjugate of claim 1, wherein B is —CH$_2$—CH$_2$—.

4. The conjugate of claim 1, wherein B is —CH$_2$—CH$_2$— and Z is C=O.

5. The conjugate of claim 1, wherein L is hydroxy or oxo, M is hydrogen or hydroxy, N is hydrogen, B is —CH$_2$—CH$_2$— and Z is C=O.

6. The conjugate of claim 1, wherein L is hydroxy, M is hydroxy, N is hydrogen, B is —CH$_2$—CH$_2$— and Z is C=O.

7. The conjugate of claim 1, wherein the fatty acid derivative is unoprostone isopropyl.

8. The conjugate of claim 1, wherein the alkyl substituted polylactide compound is having the structure:

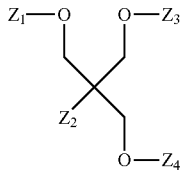

wherein Z$_2$ is selected from the group consisting of —CH$_3$ and —CH$_2$—O—Z$_5$; and wherein Z$_1$, Z$_3$, Z$_4$, and Z$_5$, each independently has the structure:

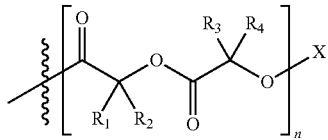

wherein R$_1$, R$_2$, R$_3$, and R$_4$ are each independently selected from the group consisting of alkyl, H, alkenyl and alkylaryl; wherein n is 1 to 100; wherein X is hydrogen, —C(O)—CH=CH$_2$ or any other functional or crosslinking group.

9. The conjugate of claim 8, wherein n is 1 to 75.

10. The conjugate of claim 8, wherein n is 1 to 50.

11. The conjugate of claim 8, wherein R$_1$ and R$_3$ are hydrogen; and R$_2$ and R$_4$ are straight or branched C1-6 alkyl.

12. The conjugate of claim 8, wherein R$_2$ and R$_4$ are —(CH$_2$)$_m$—CH$_3$, wherein m is from 0 to 20.

13. The conjugate of claim 12, wherein m is from 0 to 12.

14. The conjugate of claim 8, wherein Z$_2$ is —CH$_3$; R$_1$ and R$_3$ are hydrogen; R$_2$ and R$_4$ are —(CH$_2$)$_m$—CH$_3$, wherein m is from 0 to 20; and X is hydrogen.

15. The conjugate of claim 8, wherein Z$_2$ is —CH$_3$; R$_1$ and R$_3$ are hydrogen; R$_2$ and R$_4$ are —(CH$_2$)$_m$—CH$_3$, wherein m is from 0 to 12; and X is —C(O)—CH=CH$_2$.

16. The conjugate of claim 8, wherein Z$_2$ is —CH$_2$—O—Z$_5$; R$_1$ and R$_3$ are hydrogen; R$_2$ and R$_4$ are —(CH$_2$)$_m$—CH$_3$, wherein m=0 or m=5; and X is hydrogen.

17. The conjugate of claim 8, wherein Z$_2$ is —CH$_2$—O—Z$_5$; R$_1$ and R$_3$ are hydrogen; R$_2$ and R$_4$ are —(CH$_2$)$_m$—CH$_3$, wherein m=0 or m=5; and X is —C(O)—CH=CH$_2$.

18. The conjugate of claim 1, wherein the alkyl substituted polylactide compound is having the structure:

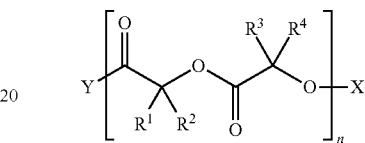

wherein R$^1$, R$^2$, R$^3$, and R$^4$ are each independently selected from the group consisting of alkyl, H, alkenyl and alkylaryl; wherein n is 1 to 100; wherein X is hydrogen or —C(O)—CH=CH$_2$ or any other functional or crosslinking group; and Y is selected from the group consisting of —OH, an alkoxy, benzyloxy and —O—(CH$_2$—CH$_2$—O)$_p$—CH$_3$; and wherein p is 1 to 700.

19. The conjugate of claim 18, wherein n is 1 to 75.

20. The conjugate of claim 18, wherein n is 1 to 50.

21. The conjugate of claim 18, wherein p is 1 to 250.

22. The conjugate of claim 18, wherein R$^1$ and R$^3$ are hydrogen; and R$^2$ and R$^4$ are straight or branched C1-6 alkyl.

23. The conjugate of claim 18, wherein Y is —O—(CH$_2$—CH$_2$—O)$_p$—CH$_3$.

24. The conjugate of claim 18, wherein R$^2$ and R$^4$ are —(CH$_2$)$_m$—CH$_3$, wherein m is from 0 to 20.

25. The conjugate of claim 24, wherein m is from 0 to 12.

26. The conjugate of claim 1, wherein the conjugate is injectable.

27. The conjugate of claim 1, wherein the conjugate is formulated for parenteral administration.

28. The conjugate of claim 1, wherein the conjugate is formulated for eye local administration.

29. A pharmaceutical composition comprising a conjugate comprising the conjugate of claim 1.

* * * * *